United States Patent
Mihlin et al.

(10) Patent No.: US 9,858,691 B2
(45) Date of Patent: Jan. 2, 2018

(54) STATISTICAL DATA ACQUISITION MODEL FOR GPU BASED MLEM JOINT ESTIMATION OF TISSUE ACTIVITY DISTRIBUTION AND PHOTON ATTENUATION MAP FROM PET DATA

(71) Applicant: The Board of Trustees of the Leland Stanford Junior University, Palo Alto, CA (US)

(72) Inventors: Alexander Mihlin, Stanford, CA (US); Craig S. Levin, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 74 days.

(21) Appl. No.: 14/815,353

(22) Filed: Jul. 31, 2015

(65) Prior Publication Data

US 2017/0032545 A1 Feb. 2, 2017

(51) Int. Cl.
| | | |
|---|---|---|
| *G06T 11/00* | (2006.01) | |
| *A61B 6/00* | (2006.01) | |
| *G01T 1/29* | (2006.01) | |
| *G06T 1/20* | (2006.01) | |
| *A61B 6/03* | (2006.01) | |

(52) U.S. Cl.
CPC ............ *G06T 11/008* (2013.01); *A61B 6/037* (2013.01); *G01T 1/2985* (2013.01); *G06T 1/20* (2013.01); *G06T 2207/10004* (2013.01); *G06T 2207/10104* (2013.01)

(58) Field of Classification Search
None
See application file for complete search history.

(56) References Cited

U.S. PATENT DOCUMENTS

| | | | |
|---|---|---|---|
| 8,299,438 B2 | 10/2012 | Fenchel et al. | |
| 8,716,669 B2 | 5/2014 | Miyaoka et al. | |
| 8,913,810 B2 | 12/2014 | Panin et al. | |
| 2010/0074501 A1* | 3/2010 | Ladebeck | G01R 33/481 382/131 |
| 2011/0303835 A1* | 12/2011 | Fenchel | A61B 6/037 250/252.1 |
| 2013/0028496 A1* | 1/2013 | Panin | G06T 11/006 382/131 |
| 2014/0328532 A1 | 11/2014 | Sun | |

(Continued)

OTHER PUBLICATIONS

A. Rezaei, M. Defrise and J. Nuyts, "ML-Reconstruction for TOF-PET With Simultaneous Estimation of the Attenuation Factors," in IEEE Transactions on Medical Imaging, vol. 33, No. 7, pp. 1563-1572, Jul. 2014. doi: 10.1109/TMI.2014.2318175.*

*Primary Examiner* — Utpal Shah
(74) *Attorney, Agent, or Firm* — Lumen Patent Firm (57) ABSTRACT

We provide improved maximum likelihood expectation maximization (MLEM) joint estimation of emission activity and photon attenuation from positron emission tomography (PET) data. Lines of response (LOR) are divided along their length into cells having equal length. MLEM computations assume all intersections between LOR cells and voxels have an intersection length of the LOR cell length. This way of discretizing the problem has the significant advantage of leading to MLEM update equations that have a closed form exact solution, which is important for fast, accurate and robust estimation.

5 Claims, 9 Drawing Sheets

(56) References Cited

U.S. PATENT DOCUMENTS

2014/0355855 A1\* 12/2014 Miao ............... A61B 5/721
      382/131
2015/0036789 A1\* 2/2015 Panin ............... A61B 6/5235
      378/4
2015/0119694 A1   4/2015 Mihlin et al.

\* cited by examiner

STATISTICAL DATA ACQUISITION MODEL FOR GPU BASED MLEM JOINT ESTIMATION OF TISSUE ACTIVITY DISTRIBUTION AND PHOTON ATTENUATION MAP FROM PET DATA

FIELD OF THE INVENTION

This invention relates to analysis of positron emission tomography (PET) data.

BACKGROUND

Quantitative PET requires knowledge of the intra-patient photon attenuation map in order to relate observed PET emission activity to the actual PET emission activity within the patient. Although the photon attenuation map can be obtained via a separate scan, such separate scanning is clearly undesirable. Accordingly, methods for estimating both emission activity and photon attenuation from PET data have been considered.

One such approach is considered by the present inventors in US 2015/0119694, filed on Oct. 30, 2014 and hereby incorporated by reference in its entirety. In this work, maximum likelihood expectation maximization (MLEM) is considered for the joint estimation of emission activity and photon attenuation from PET data.

SUMMARY

However, it remains challenging to implement MLEM joint estimation of emission activity and photon attenuation from PET data in a computationally robust and sufficiently rapid manner. The present work addresses these issues by providing an improved numerical formulation of such MLEM joint estimation.

Figure 1A:
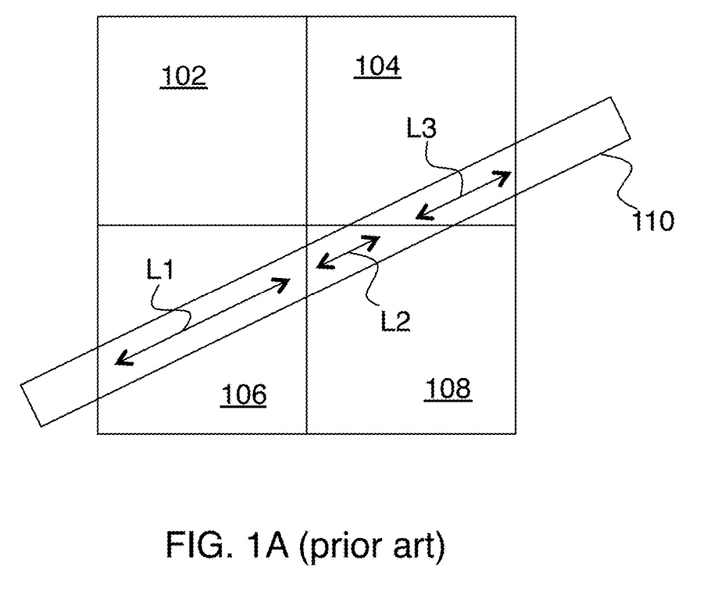
FIG. 1A shows a conventional computational geometry for PET imaging.
Figure 1B:
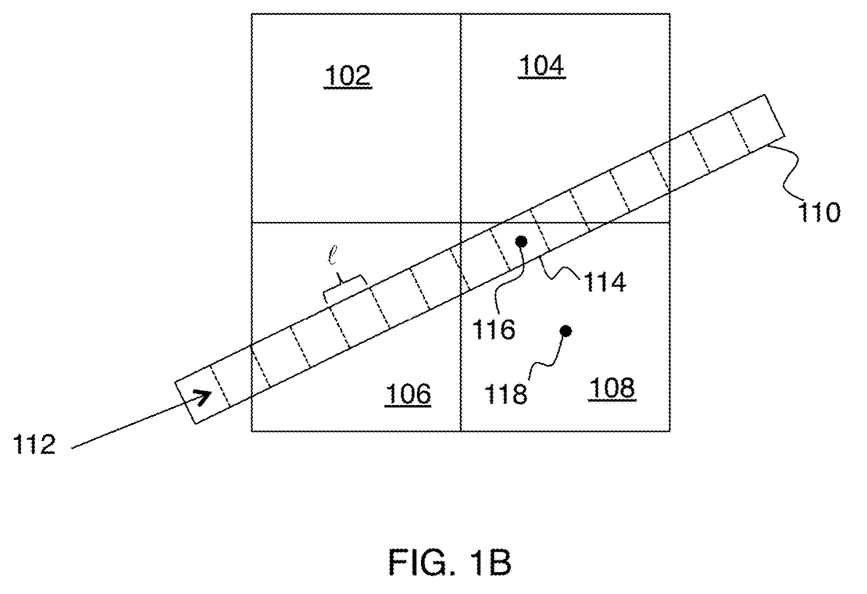
FIG. 1B shows computational geometry for PET imaging according to principles of the invention.

One important idea of the present approach can be appreciated by considering FIGS. 1A-B. A quantity that effectively needs to be computed for MLEM joint estimation is the length of an intersection between a line of response (LOR) and a voxel. FIG. 1A shows voxels 102, 104, 106 and 108 and a line of response 110 configured such that LOR 110 intersects voxels 106, 108 and 104 with intersection lengths L1, L2 and L3 respectively. Although the geometry of FIG. 1A can be used to calculate the intersection lengths, such calculations can be time consuming. More importantly, the resulting numerical method with variable LOR-voxel intersection lengths has the undesirable feature of lacking a closed form solution for the update equations (see Appendix B).

FIG. 1B shows how this problem is alleviated in the present approach. Here line of response 110 is divided along its length into cells 112 having equal length l. MLEM computations assume all intersections between LOR cells and voxels have an intersection length of l. This way of discretizing the problem has the significant advantage of leading to update equations that have a closed form solution. It effectively amounts to calculating LOR-voxel intersection lengths by counting the number of LOR cells deemed to be within the relevant voxel. The most significant feature of this approach is that it completely eliminates variable LOR-voxel intersection lengths from the numerical formulation in a sound manner (i.e., this model becomes exact in the limit of infinitesimal LOR width and LOR cell length).

DETAILED DESCRIPTION

A) General Principles

An exemplary embodiment of the invention is a method of image reconstruction for positron emission tomography, where the method includes:

1) obtaining raw PET data from a PET scanner; and
2) analyzing the raw PET data to provide estimates of both emission activity and photon attenuation;

Here analyzing the raw PET data is performed via maximum likelihood expectation maximization (MLEM). A first set of MLEM coordinates relates to voxels in a PET image. A second set of MLEM coordinates is defined by a partition of each line of response (LOR) into LOR cells having equal length l (e.g., as shown on FIG. 1B). MLEM computations assume all intersections between LOR cells and voxels have an intersection length of l.

In preferred embodiments, computations for MLEM are performed on a graphics processing unit (GPU). Parameters for MLEM update computations can be performed by traversing lines of response only twice per iteration for efficient incremental updates.

B) Detailed Example

B1) Introduction

Quantitative Positron Emission Tomography (PET) requires the knowledge of the intra-patient photon attenuation map. This attenuation map may be obtained via a priori transmission scan. However, a transmission scan exposes the patient to additional ionizing radiation, prolongs the overall scan time and requires the availability of equipment, such as an x-ray CT system in line with the PET system. Moreover, the imperfect registration and photon energy differences between the transmission- and emission scans, result in undesirable image artifacts. In addition to these technical challenges, a transmission scan is unavailable in combined PET and Magnetic Resonance Imaging (PET/MRI) scanners, while estimating photon attenuation coefficients using MRI data has proven to be challenging and inaccurate in many cases.

To avoid these shortcomings, several groups proposed methods for obtaining the attenuation map from the PET emission data alone. These include MLAA, which iteratively applies a fixed photon attenuation MLEM emission activity distribution update, and a fixed emission activity MLTR photon attenuation map update. Similarly, the minorizing function algorithm also updates the emission activity distribution and photon attenuation map independently, but maximizes the PET likelihood's lower bound instead of the likelihood itself, which simplifies the update equations.

Recently, our research group proposed the Expectation Maximization Activity Attenuation (EMAA) algorithm—a Maximum Likelihood Expectation Maximization (MLEM), method for joint estimation of emission activity distribution and photon attenuation map in PET. The main difference of this approach from the above methods is that there is a joint-, as opposed to independent, emission activity distribution- and photon attenuation map update. This difference is akin to that between coordinate- and gradient ascent maximization. Moreover, compared to those other methods, the EMAA algorithm is appealing for the following reasons: (i) It guarantees monotonic likelihood increase to a local extrema, (ii) does not require arbitrary parameters, and (iii) guarantees the positivity of the estimated distributions.

These advantages follow from the use of the MLEM algorithm. PET emission activity distribution alone is routinely reconstructed using a particular version of MLEM. However, when the photon attenuation map is added into the estimation task, this version results in a non separable likelihood function, which is difficult to maximize. Conversely, the proposed MLEM method results in a separable likelihood function, which simplifies maximization. It is based on a new set of latent random variables, similar to that proposed by other workers for CT (computed tomography) and for SPECT (single photon emission CT).

Furthermore, in order to facilitate practical implementation, we propose a discrete Poisson data acquisition model that enables: (i) Efficient graphics processing unit (GPU) based formulation, in conjunction with accurate system matrix- and line of response (LOR)/computational cell intersection length computation, and (ii) A closed form exact solution for the MLEM update equations, which is essential for an accurate and robust photon attenuation map estimation.

This section is organized as follows: the proposed data acquisition model, EMAA algorithm, its numerical formulation, and the experimental setup are explained in Section B2. The experimental results are described in Section B3. Section B4 contains a discussion, and Section B5 a short conclusion. Some additional mathematical derivations are given in Appendices A and B.

B2) Methods
B2a) Data Acquisition Model

The following section describes the discrete data acquisition model illustrated in FIG. 1B. The estimated emission activity per unit volume and photon attenuation per unit length are assigned to the voxel centers of a Cartesian three dimensional grid. Here 102, 104, 106 and 108 are voxels. Each LOR 110 is divided into equal size "cells" 112, and the cell emission activity and photon attenuation (e.g., at location 116 in cell 114) are approximated by the corresponding parameters at the voxel containing the cell center (i.e., at center 118 of voxel 108).

The model is coarse when the LORs are wide- or the cells are long compared with the voxels, but becomes exact in the infinitesimal LOR width and cell length limit. Moreover, the model inaccuracy is only significant for details on the voxel scale, which are typically blurred due to discretization.

Since the computational cells are LOR aligned, as opposed to Cartesian, geometric system matrix parameters can be quickly and accurately computed. Moreover, the constant LOR/cell intersection length enables an exact closed form solution of the photon attenuation map update equations, which accelerates and stabilizes the computation. Furthermore, the estimation time scales linearly with field of view resolution. For example, doubling the number of voxels along all axes and appropriately halving the cell lengths, results in only twice the estimation time. The reason for this is the estimation time dependence on the number of cells, as opposed to voxels. Particularly, this makes it independent of the field of view dimensionality when the LORs number is constant.

B2b) EMAA Algorithm

Figure 2:
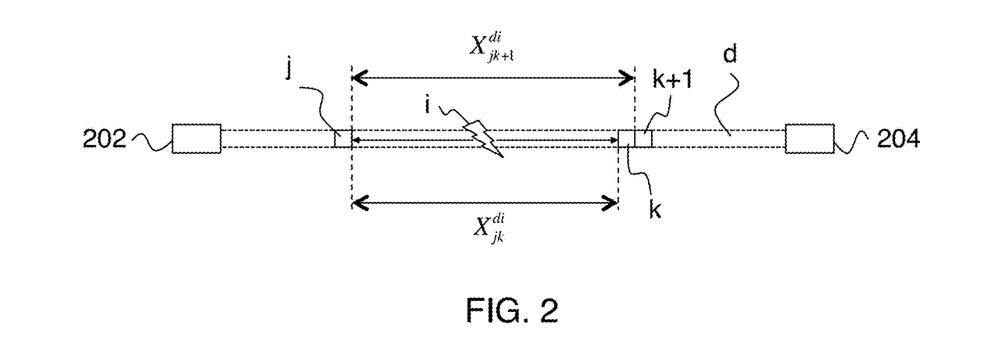
FIG. 2 shows the definition of random variables used to formulate the present approach.

The following section introduces the EMAA algorithm. FIG. 2 shows the definition of the random variables $X_{jk}^{di}$. Here detectors 202 and 204 define a line of response d, and $X_{jk}^{di}$ is the number of photon pairs reaching cells j and k along LOR d, after being emitted in cell i. Particularly, $X_{ii}^{di}$ denotes the total number of photons emitted from cell i into LOR d.

Some further notation definitions are listed below:
d—LOR index within the complete-, not just observed, set.
N—Number of cells along a particular LOR (the LOR index d is implicit).
i,j,k=1 . . . N—Cell indices along a particular LOR.
ξ—Voxel index.
ξ(d,i)—The index of the voxel that contains the center of cell i in LOR d.
m—Iteration index.
$n_d$—Number of counts along LOR d.
I—The indicator function.
θ—Emission activity per unit volume.
μ—Photon attenuation per unit length.
$\theta_{di} \equiv \theta_{\xi(d,i)}$, $\mu_{di} \equiv \mu_{\xi(di)}$
l—LOR/cell intersection length.
$\gamma_{ij}^d$—Photon transition probability along LOR d between cells i and j:

$$\gamma_{ij}^d = e^{-l\sum_k^{i<k<j} \mu_{dk}}.$$

Particularly: $\gamma_{ii}^d = \gamma_{ii+1}^d = 1$.
$c_{di}$—Cell i/LOR d system matrix element times the cell volume. More specifically, $c_{di}$ is defined as the probability of a photon pair emitted inside cell i to be detected inside LOR d, in the absence of photon attenuation.
$I_{di\xi}=1(0)$ if the center of cell i in LOR d is inside(outside) voxel ξ.
L—Acquired signal likelihood.
L*—The effective likelihood that is maximized.

The algorithm maximizes the following Poisson probability of detecting the true coincidences n, with respect to the emission activity distribution, θ, and photon attenuation map, μ:

$$P(\theta, \mu; n) = \prod_d Pois\left(e^{-l\sum_i \mu_{di}} \sum_i \theta_{di} c_{di}\right) \quad (1)$$

$$= \prod_d \frac{\exp\left(e^{-l\sum_i \mu_{di}} \sum_i \theta_{di} c_{di}\right)\left(e^{-l\sum_i \mu_{di}} \sum_i \theta_{di} c_{di}\right)^{n_d}}{n_d!}$$

The present MLEM method is based on the latent random variables, $X_{jk}^{di}$, defined above. Similar variables were proposed by others for CT and for SPECT [15]. These variables are independent for different d or i. The dependence for the same d and i arises since the number of photons cannot increase downstream (e.g. $X_{jk}^{di} \geq X_{jk+1}^{di}$). The relevant marginal distributions are given by the following expressions:

$$X_{ii}^{di} \sim \text{Pois}(\theta_{di} c_{di}) \quad (2)$$

$$X_{jk+1}^{di} | X_{jk}^{di} \sim \text{Bin}(X_{jk}^{di}, e^{-\mu_{dk} l})$$

$$X_{j-1k}^{di} | X_{jk}^{di} \sim \text{Bin}(X_{jk}^{di}, e^{-\mu_{dj} l}) \quad (3)$$

Figure 3:
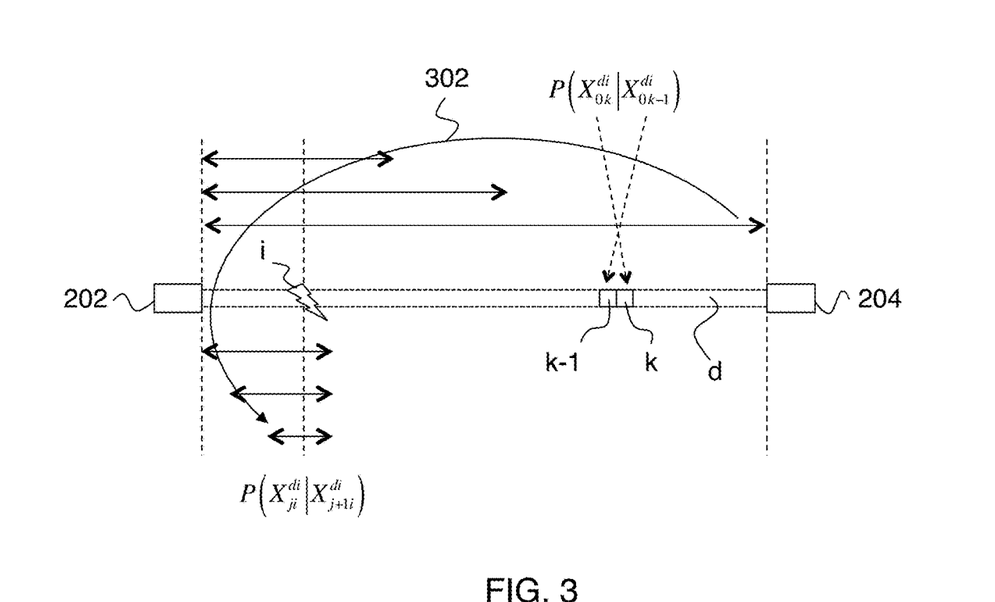
FIG. 3 schematically shows the construction of Eq. (4).

FIG. 3 shows construction of the probability function in Eq. (4) by a product of conditional probabilities of the form $P(X_{ji}^{di} | X_{j+1i}^{di})$ using Bayes' rule. The voxels j, k in the corresponding estimated $X_{jk}^{di}$ are indicated by the horizontal arrows. The product order in Eq. (4) is indicated by the arrow 302. Since each conditional probability contains a single photon attenuation coefficient, the likelihood function is separable.

As illustrated in FIG. 3, the distribution of the dependent variables $X^{di}$ is given by the following expression:

$$\begin{aligned}
P(X^{di}) &= P(X_{0N+1}^{di}, \ldots, X_{0i+1}^{di}, X_{1i+1}^{di}, \ldots, X_{i-1i+1}^{di}, X_{ii}^{di}) \quad (4)\\
&= P(X_{0N+1}^{di} | X_{0N}^{di}) P(X_{0N}^{di}, \ldots)\\
&= P(X_{0N+1}^{di} | X_{0N}^{di}) \cdot \ldots \cdot P(X_{0i+2}^{di} | X_{0i+1}^{di}) \cdot\\
&\quad P(X_{0i+1}^{di} | X_{1i+1}^{di}) \cdot \ldots \cdot P(X_{i-1i+1}^{di} | X_{ii}^{di}) \cdot P(X_{ii}^{di})
\end{aligned}$$

Using Eq. (4) and the independence properties of $X_{jk}$ mentioned above, the complete variable set is distributed as follows:

$$P(X) = \prod_{di} P(X^{di}) \quad (5)$$

Following the standard MLEM derivation, the likelihood, L, is given by the following expression:

$$L \equiv \ln\left[\prod_d P(n_d)\right] = \sum_d \ln\left[\sum_X P(X, n_d)\right] \quad (6)$$

where $P(n_d)$, the probability of observing $n_d$ counts along LOR d, is given by Eq. (1), and $P(X, n_d) = P(X)$ since $n_d = \Sigma_i X_{0N+1}^{di}$. Given the m-th iteration parameters $\theta^m$, $\mu^m$, the following Jensen's inequality holds:

$$\begin{aligned}
L(\theta, \mu) &= \ln\left[\sum_X P(X | n; \theta^m, \mu^m) \frac{P(X, n; \theta, \mu)}{P(X | n; \theta^m, \mu^m)}\right] \quad (7)\\
&\geq \sum_X P(X | n; \theta^m, \mu^m) \ln\left[\frac{P(X, n; \theta, \mu)}{P(X | n; \theta^m, \mu^m)}\right]\\
&= E[\ln P(X; \theta, \mu) | n; \theta^m, \mu^m] + f(n, \theta^m, \mu^m)
\end{aligned}$$

where E denotes expectation. This inequality forms the basis for the MLEM optimization method described below. Particularly, the likelihood's lower bound given in the second line is maximized in each iteration. The explicit form of the function f is unimportant since it does not depend on θ and µ, and hence excluded from the maximization process.

Omitting the terms irrelevant to maximization with respect to θ and µ, and substituting Eqs. (2)-(4) into Eq. (5), the effective likelihood, L*, the expectation of which is to be maximized, is given by the following expression:

$$\begin{aligned}
L^*(\theta, \mu) &= \ln P(X; \theta, \mu) = \sum_{di}\Big\{-\theta_{di} c_{di} + X_{ii}^{di} \ln \theta_{di} + \quad (8)\\
&\quad (X_{ii}^{di} - X_{i-1i+1}^{di}) \ln(1 - e^{-\mu_{di} l}) - X_{i-1i+1}^{di} \mu_{di} l +\\
&\quad \sum_j \left([(X_{ji+1}^{di} - X_{j-1i+1}^{di}) \ln(1 - e^{-\mu_{dj} l}) - X_{j-1i+1}^{di} \mu_{dj} l] I_{j<i} + [\right.\\
&\quad \left.(X_{0j}^{di} - X_{0j+1}^{di}) \ln(1 - e^{-\mu_{dj} l}) - X_{0j+1}^{di} \mu_{dj} l] I_{j>i}\right)\Big\} + g(X)
\end{aligned}$$

where the explicit form of the function g(X) is unimportant since it does not depend on θ and µ, and hence excluded from the maximization process. Each iteration includes two steps, denoted "Expectation" and "Maximization". In a given iteration m, the Expectation step calculates the form of $[L^*(\theta, \mu) | n; \theta^m, \mu^m]$, and the Maximization step calculates the new parameters, $\theta^{m+1}$, $\mu^{m+1}$, that maximize this expectation:

$$\{\theta^{m+1}, \mu^{m+1}\} = \operatorname*{argmax}_{\theta, \mu} E[L^*(\theta, \mu) | n; \theta^m, \mu^m] \quad (9)$$

The expectation in Eq. (9) is given by substituting the following expression for $X_{jk}^{di}$ (Appendix. A) into Eq. (8):

$$\begin{aligned}
\hat{X}_{jk}^{di} &\equiv E(X_{jk}^{di} | n; \theta^m, \mu^m) \quad (10)\\
&= \theta_{di}^m c_{di}\left(\frac{n_d}{\sum_j \theta_{dj}^m c_{dj}} + \gamma_{jk}^{dm} - \gamma_{0N+1}^{dm}\right)
\end{aligned}$$

As opposed to Eq. (6), the likelihood in Eq. (8) is additively-separable. That is, each summand depends on a single reconstructed parameter $\theta_{di}$ or $\mu_{di}$, which simplifies the maximization in Eq. (9). This maximization results (Appendix. B) in a system of independent, one dimensional, update equations:

$$\theta_{\xi}^{m+1} = \frac{\theta_{\xi}^m}{\sum_{di} I_{di\xi} c_{di}} \sum_{di} I_{di\xi} c_{di}\left(\frac{n_d}{\sum_j c_{dj} \theta_{dj}^m} + 1 - \gamma_{0N+1}^{dm}\right) \quad (11)$$

$$\mu_{\xi}^{m+1} = \frac{1}{l} \ln\left(\frac{[1 - e^{-\mu_{\xi}^m l}] \sum_{dij} I_{di\xi} \theta_{dj}^m c_{dj} [\gamma_{0i}^{dm} I_{j<1} + \gamma_{ij+1}^{dm} I_{j\geq i}]}{\sum_{di} I_{di\xi}\left\{e^{-\mu_{\xi}^m l} \sum_j \theta_{dj}^m c_{dj}[\gamma_{0i}^{dm} I_{j<1} + \gamma_{ij+1}^{dm} I_{j\geq i}] + n_d - \gamma_{0N+1}^{dm} \sum_j \theta_{dj}^m c_{dj}\right\}} + 1\right) \quad (12)$$

These equations have the following desirable properties:
1) In the absence of photon attenuation, $\gamma_{0N+1}^{dm} = 1$, and the emission activity update equation (11) reduces to a known result in the literature.
2) Eqs. (11) and (12) converge for voxel ξ if and only if $\Sigma_{di} I_{di\xi} n_d = \Sigma_{di} I_{di\xi} \gamma_{0N+1}^{dm} \Sigma_j \theta_{dj} c_{dj}$ or $\mu_\xi = \theta_\xi = 0$. That is, if the total observed and expected count numbers in the LORs intersecting voxel ξ are equal.
3) Since $\gamma_{0N+1}^{dm} \leq \gamma_{jk}^{dm} \leq 1$, the emission activity distribution and photon attenuation map are guaranteed to remain non-negative.

B2c) Convergence

The following section proves that the present method is guaranteed to converge to a local likelihood extrema.

Using the notations of Eq. (7), let:

$$Q_m(\theta,\mu) = E[L^*(\theta,\mu)|n;\theta^m,\mu^m] + f(n,\theta^m,\mu^m) \quad (13)$$

Following the general MLEM convergence argument:

$$L(\theta^{m+1},\mu^{m+1}) \geq Q_m(\theta^{m+1},\mu^{m+1}) \geq Q_m(\theta^m,\mu^m) = L(\theta^m,\mu^m) \quad (14)$$

where the first relation follows from Eq. (7), the second is due to Eq. (9), and the third is obtained by applying Bayes' law to Eq. (7). Since according to Eq. (14), the likelihood does not decrease with iteration number, the algorithm monotonically converges to some point $(\theta^*, \mu^*)$. To show that this is a local extrema of L, note that since from Eq. (7):

$$L(\theta,\mu) \geq Q_m(\theta,\mu) \quad \forall \theta,\mu L(\theta^m,\mu^m) = Q_m(\theta^m,\mu^m)$$

the functions $Q_m$ and L are tangential to each other at $(\theta^m, \mu^m)$. Using this property, and noting that convergence is reached on iteration m if $(\theta^m, \mu^m) = (\theta^*, \mu^*) = (\theta^{m+1}, \mu^{m+1})$:

$$\nabla L(\theta^*, \mu^*) = \nabla Q_m(\theta^*, \mu^*) = \nabla Q_m(\theta^{m+1}, \mu^{m+1}) = \nabla \max_{\theta,\mu} Q_m(\theta, \mu) = 0 \quad (15)$$

which completes the proof.

B2d) Numerical Formulation

The following section describes a numerical formulation of EMAA. An iteration may be completed with two traversals per LOR, by reformulating the emission activity distribution and photon attenuation map update equations (11), (12) in terms of the following quantities:

$$S_i^{dm} \equiv \Sigma_j \theta_{dj}^m c_{dj} \gamma_{ij+1}^{dm} I_{j \geq i} \quad (16)$$

$$D_i^{dm} \equiv \Sigma_j \mu_{dj}^m I_{j<i} \quad (17)$$

$$K_i^{dm} \equiv \Sigma_j \theta_{dj}^m c_{dj} I_{j<i} \quad (18)$$

Figure 4:
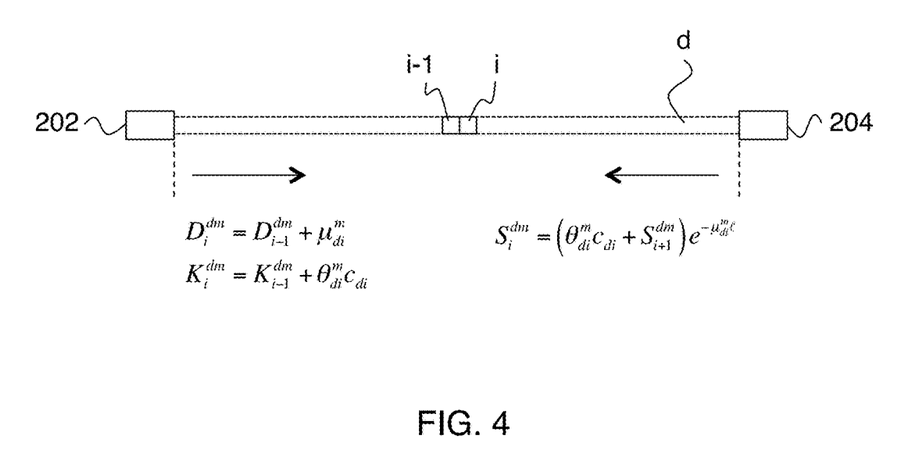
FIG. 4 shows how parameters for joint attenuation and emission estimation can be incrementally calculated.

As illustrated in FIG. 4, these may be calculated incrementally using the following connections:

$$S_i^{dm} = (\theta_{di}^m c_{di} + S_{i+1}^{dm}) e^{-\mu_{di}^m l} \quad (19)$$

$$D_i^{dm} = D_{i-1}^{dm} + \mu_{di}^m \quad (20)$$

$$K_i^{dm} = K_{i-1}^{dm} + \theta_{di}^m c_{di} \quad (21)$$

where $S_{N+1}^{dm} = D_0^{dm} = K_0^{dm} = 0$. Parameters $D^{dm}$ and $K^{dm}$ are calculated by a positively directed LOR traversal, while $S^{dm}$ is calculated by a second, oppositely directed, traversal.

These connections define the following auxiliary quantities:

$$R_\xi^m \equiv \sum_{di} I_{di\xi} \left( S_i^{dm} + e^{-lD_i^{dm}} K_i^{dm} \right) \quad (22)$$

$$G_\xi^m \equiv \sum_{di} I_{di\xi} \left( n_d - e^{-lD_{N+1}^{dm}} K_{N+1}^{dm} \right) \quad (23)$$

$$A_\xi^m \equiv \sum_{di} I_{di\xi} c_{di} \left( \frac{n_d}{K_N^{dm}} + 1 - e^{-lD_{N+1}^{dm}} \right) \quad (24)$$

$$P_\xi \equiv \sum_{di} I_{di\xi} c_{di} \quad (25)$$

where the normalization factor $P_\xi$ is computed only once. Update equations (11) and (12) are now given by the following expressions:

$$\theta_\xi^{m+1} = \frac{\theta_\xi^m}{P_\xi} A_\xi \quad (26)$$

$$\mu_\xi^{m+1} = \frac{1}{l} \ln\left[ 1 + \frac{(1 - e^{-l\mu_\xi^m}) R_\xi^m}{G_\xi^m + e^{-l\mu_\xi^m} R_\xi^m} \right] \quad (27)$$

Notably, the LOR oriented data acquisition model of Section B2a provides a natural way for the directional LOR traversal in Eqs. (19)-(21). The computation of Eqs. (26) and (27) is summarized below in Algorithm 1.

```
 1:    L ← 0;
 2:    for all voxels ξ do
 3:        A_ξ ← 0;
 4:        G_ξ ← 0;
 5:        R_ξ ← 0;
 6:    end for
 7:    for all detected LORs d do
 8:        K ← 0;
 9:        D ← 0;
10:        for LOR cell i = 1 to N_d do
11:            G_ξ(d,i) ← G_ξ(d,i) + n_d;
12:            D ← D + μ_di^m;
13:            K ← K + θ_di^m c_di;
14:        end for
15:        L ← n_d (ln K − lD);
16:        for LOR cell i = 1 to N_d do
17:            A_ξ(d,i) ← A_ξ(d,i) + c_di n_d/K;
18:        end for
19:    end for
20:    for all LORs d do
21:        K ← 0;
22:        D ← 0;
23:        for LOR cell i = 1 to N_d do
24:            R_ξ(d,i) ← e^{-Dl} K;
25:            D ← D + μ_di^m;
26:            K ← K + θ_di^m c_di^m;
27:        end for
28:        L ← L − e^{-Dl} K;
29:        S ← 0;
30:        for LOR cell i = N_d to 1 do
31:            A_ξ(d,i) ← A_ξ(d,i) + c_di (1 − e^{-lD});
32:            G_ξ(d,i) ← G_ξ(d,i) − e^{-lD} K;
33:            R_ξ(d,i) ← R_ξ(d,i) + θ_di^m c_di + S;
34:            S ← (θ_di^m c_di + S) e^{-lμ_ξ^m};
35:        end for
36:    end for
37:    for all voxels ξ do
38:        θ_ξ^{m+1} ← θ_ξ^m A_ξ/P_ξ;
39:        
              μ_ξ^{m+1} ← (1/l) ln[ 1 + (1 − e^{-lμ_ξ^m}) R_ξ / (G_ξ + e^{-lμ_ξ^m} R_ξ) ];
40:    end for
```

Algorithm 1: An MLAA iteration: calculate the new emission activity distribution and photon attenuation map, and the previous iteration's likelihood. Here the dependence of N on the LOR index d is made explicit, and a detected LOR is defined as an LOR along which at least one true photon coincidence event was detected.

One potential numerical pitfall in Algorithm 1 has to do with the floating point round off error. Particularly, each summand in Eqs. (22)-(25) may be smaller than one, while for low resolution grids, the number of summands may be large. As a result, if single, as opposed to double, precision floating point variables are used, all additions after the sum reaches $2^{24}$ will be discarded due to a round off error:

$$A_\xi + 1 := A_\xi \geq 2^{24} ? A_\xi : A_\xi + 1 \quad (28)$$

This potential error may be addressed by using double precision variables. However, we did not find this to be an issue for reasonable resolution grids, where the sums per voxel are small enough.

B2e) Numerical Experiments

The following section describes the setup of the numerical experiments included in this work:
1) Estimation of emission activity distribution only, with known photon attenuation map.
2) Estimation of photon attenuation map only, with known emission activity distribution.
3) Joint estimation of emission activity distribution and photon attenuation map.
4) Estimation of reference emission activity distributions with (i) no- and (ii) uniform photon attenuation map.

The first two experiments aim at (i) validating update equations (11) and (12), and (ii) helping understand the convergence properties of this joint estimation method. The last experiment compares joint EMAA emission activity distribution estimation, with that of emission activity distribution only when a transmission scan is unavailable.

Figure 5:
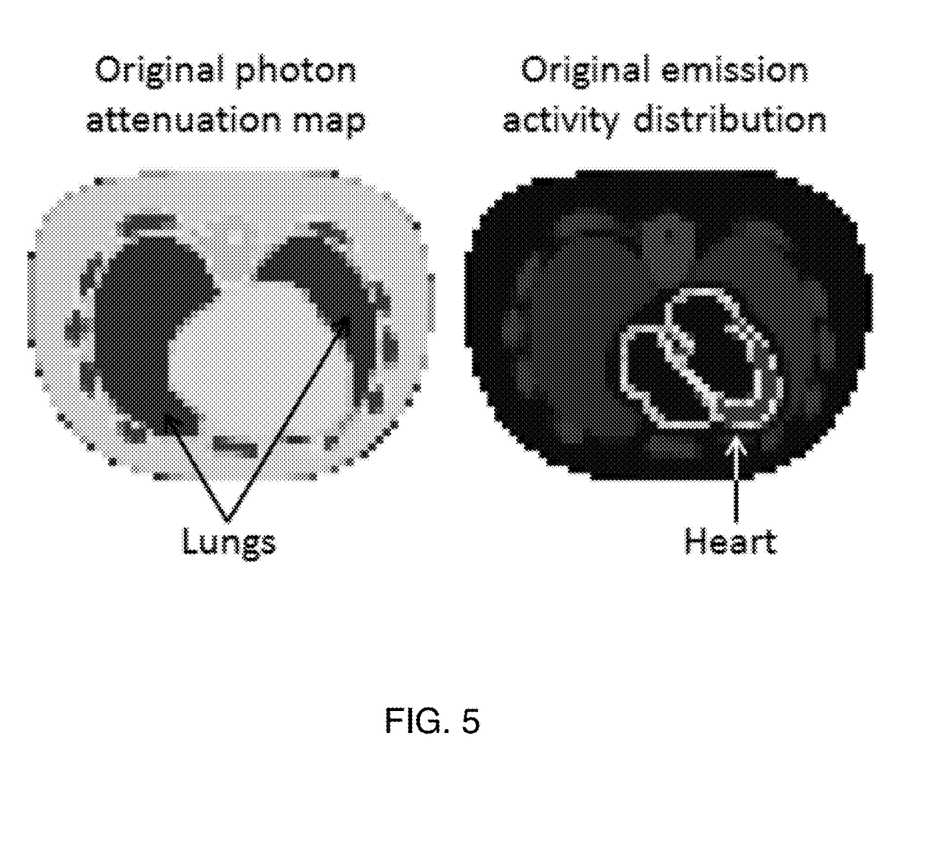
FIG. 5 shows images of a phantom used in experiments relating to the invention.

The PET dataset was computationally generated using the two dimensional 128×128 voxel thorax XCAT phantom illustrated in FIG. 5. Here the left side shows the emission activity distribution and the right side shows the photon attenuation map. Around 4M true coincidences were recorded using the Poison model of Eq. (1), with perfect energy and time resolution (random and tissue scattered coincidences were not recorded), and 100% detector efficiencies. The two dimensional detector ring was of radius 40 cm, and included 576 densely packed detectors which correspond to 165,600 LORs. Cell- and voxel lengths were equal. The initial emission activity- and photon attenuation distributions were constant inside- and zero outside the phantom. The corresponding error distributions, Err, were calculated from the estimated, Est, and exact, Exact, distributions using the following formula:

$$\text{Err} = 100 \cdot \frac{|\text{Est} - \text{Exact}|}{\text{Exact}} \quad (29)$$

where Hadamard division is implied.

B3) Results

Figure 6:
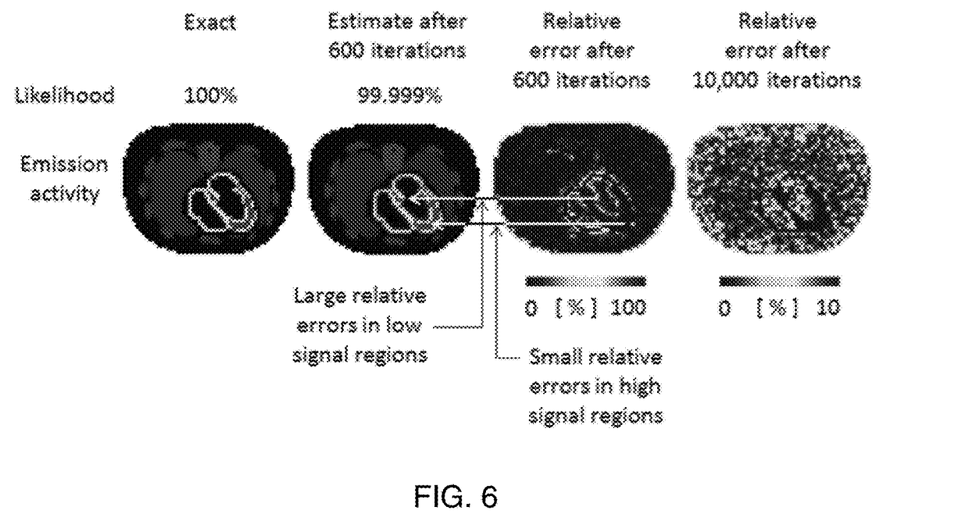
FIG. 6 shows estimates of emission activity with a known photon attenuation distribution.

The following section describes the results of the numerical experiments described in Section B2e. In all experiments, a single iteration on Nvidia's Tesla K20 GPU took about half a second. FIG. 6 illustrates an EMAA estimation of emission activity distribution only, with known photon attenuation map. Here the left side shows exact and estimated distributions, and the right side shows estimation errors. The arrows illustrate large relative errors obtained in low signal regions and small relative errors obtained in high signal regions. Reasonable convergence was observed after a few tens of iterations, and the shown estimation took five minutes. The root mean square errors (RMSE) after five minute- and one hour long estimation, were 18% and 8% respectively, and the corresponding errors in the myocardium only, were 4% and 0.3% respectively.

Figure 7:
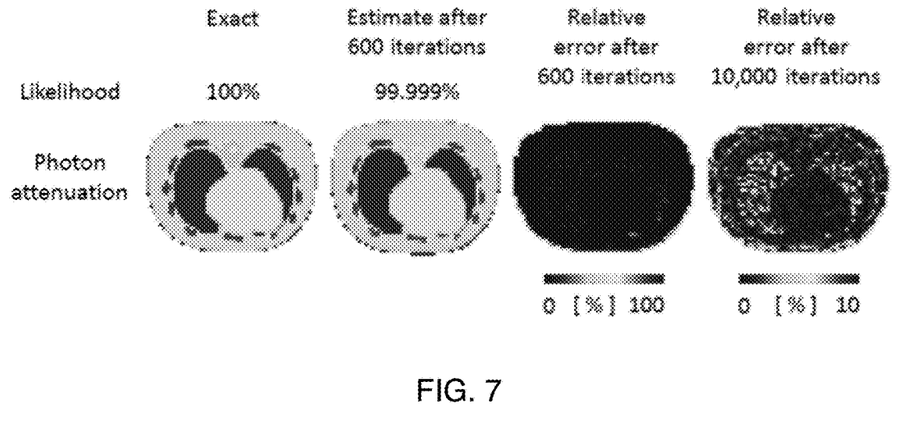
FIG. 7 shows estimates of photon attenuation with a known emission activity distribution.

FIG. 7 illustrates an EMAA estimation of photon attenuation map only, with known emission activity distribution. Here the exact and estimated maps are shown on the left, and estimation errors are shown on the right. Reasonable convergence was observed after a few tens of iterations, and the shown estimation took five minutes. The root mean square errors after five minute- and one hour long estimation, were 6% and 5% respectively.

Figure 8:
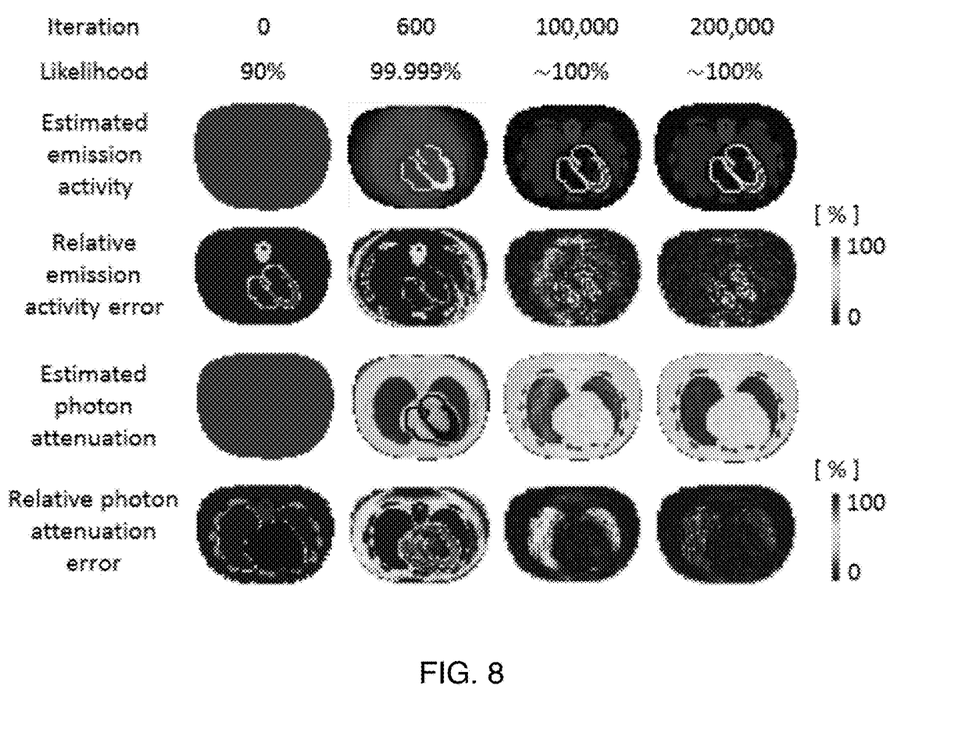
FIG. 8 shows joint estimates of emission activity and photon attenuation.

FIG. 8 illustrates the joint estimation of emission activity distribution and photon attenuation map via Algorithm 1. Here the top two rows show estimated emission activity distribution and the corresponding error image. The bottom two rows show estimated photon attenuation map and the corresponding error image. The myocardial emission activity, and the non uniform photon attenuation due to the lungs, ribs and spine are clearly visible in the estimated distributions on the right. Reasonable convergence was observed after a few tens of thousands of iterations. The emission activity distribution root mean square errors after twelve- and twenty four hour long estimation, were 20% and 15% respectively, and the corresponding errors in the myocardium only, were 10% and 6% respectively. The corresponding photon attenuation map root mean square errors were 17% and 9% respectively.

Figure 9:
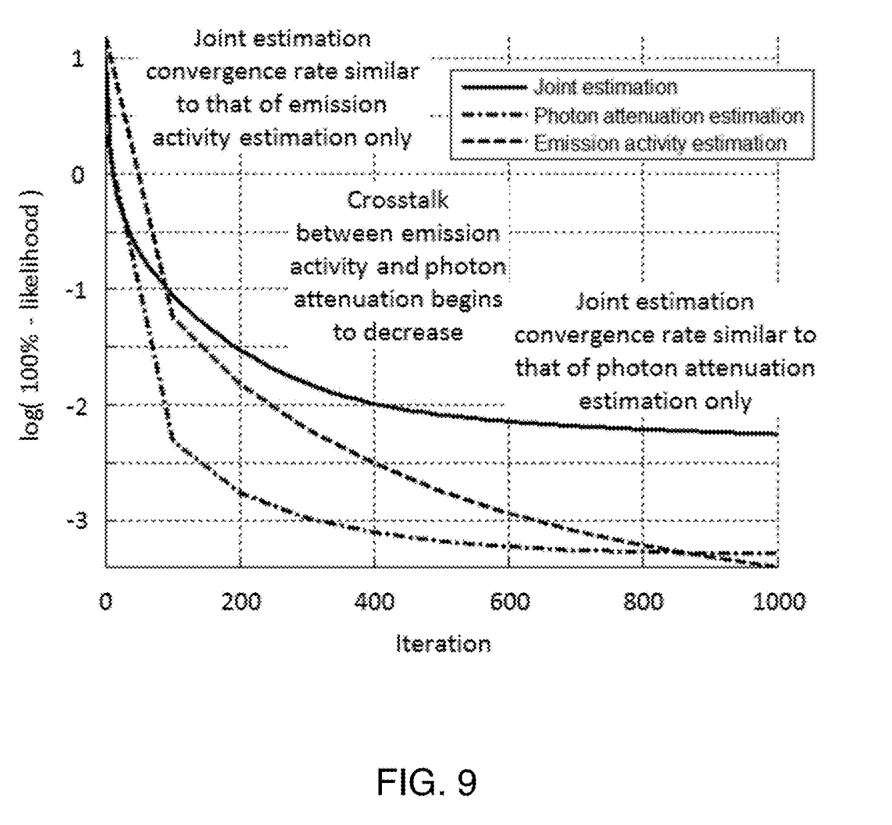
FIG. 9 shows convergence of the likelihood function.

FIG. 9 illustrates the likelihood convergence rates in the above experiments. Here the vertical axis corresponds to the logarithm of the difference between the maximal and intermediate likelihood values. The horizontal axis corresponds to the iteration index. The joint estimation (solid line) convergence rate begins similar to that of emission activity distribution only (dashed line) but with further iterations becomes similar to that of photon attenuation map only (dash-dotted line).

Figure 10:
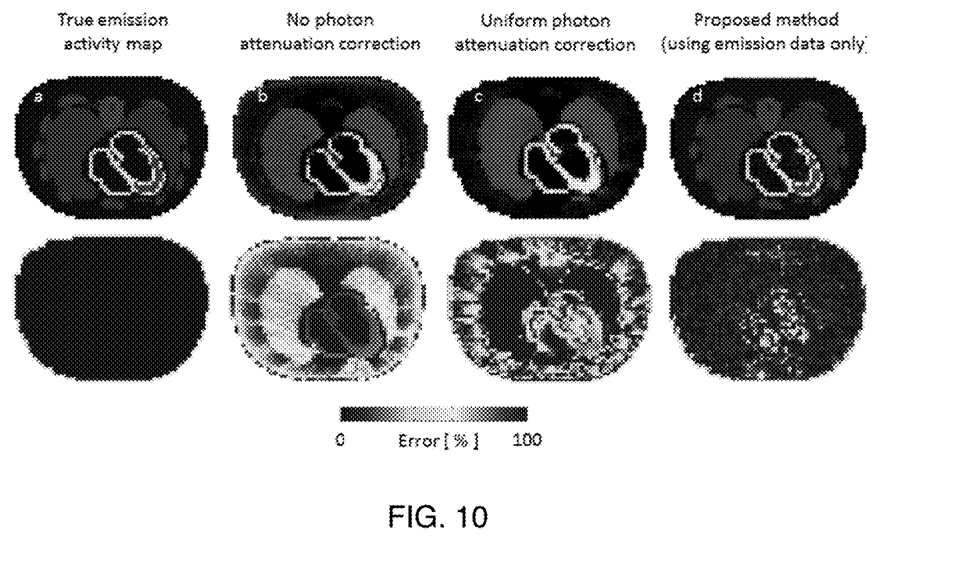
FIG. 10 shows the effect of the assumed or estimated photon attenuation map on the estimated emission activity distribution.

FIG. 10 compares the jointly estimated emission activity distribution with two common photon attenuation map guesses in the absence of a transmission scan: (i) none-, and (ii) uniform phantom, as opposed to field of view, photon attenuation map. The top row shows estimated emission activity distribution images for several photon attenuation maps: (a) known photon attenuation map, (b) no photon attenuation, (c) uniform photon attenuation, and (d) jointly estimated photon attenuation map. The bottom row shows the corresponding error distributions. Table 1 lists the corresponding myocardial emission activity distribution estimation root mean square errors, obtained according to Eq. (29).

TABLE 1

Root mean square errors in the estimation of myocardial emission activity distribution for different attenuation maps.

| Attenuation map | Myocardial RMSE [%] |
| --- | --- |
| Known (FIG. 6) | 0.1 |
| Jointly estimated ((d) of FIG. 10) | 6 |
| None ((b) of FIG. 10) | 92 |
| Uniform ((c) FIG. 10) | 41 |

B4) Discussion

FIG. 10 in conjunction with Table 1 shows that EMAA may improve the quality and accuracy of the estimated emission activity distribution in the absence of a priori photon attenuation map. Particularly, it results in an emission activity distribution root mean square error of 6%, compared with that of 41% and 92% for uniform- and zero photon attenuation maps respectively.

The current version of EMAA is too slow for clinical application. Joint estimation (FIG. 8) takes longer than a separate estimation of emission activity distribution (FIG. 6) and photon attenuation map (FIG. 7), due to the crosstalk between them illustrated in the second column of FIG. 8. As illustrated in FIG. 9, once the crosstalk is established, the convergence rate is dominated by that of the photon attenuation map, which slows down the estimation. We believe that EMAA convergence could be accelerated by reducing this crosstalk, for example via regularization or by using a photon attenuation map prior.

As illustrated in FIG. 6, the large emission activity distribution estimation errors are mainly in low signal regions, such as the heart chambers. However, since these are of small magnitude, they do not influence the accuracy and quality of the estimated distribution.

As mentioned above, random and tissue scattered coincidences were not included in the computational experiments. However, since EMAA maximizes the standard PET likelihood, these should have a similar effect as in a standard estimation of emission activity distribution only, where the photon attenuation map is estimated separately, as long as both methods converge to the same likelihood extrema. Though such convergence is not guaranteed since the joint likelihood is not concave without additional time of flight (TOF) information, as illustrated in FIG. 8, our numerical experiments indicate that EMAA estimation robustly converges to the original emission activity distribution and photon attenuation map, with root mean square errors of 15% and 9% respectively.

We expect that the present method may be accelerated by up to 50× via Ordered Subset Expectation Maximization (OSEM). Additionally, since it maximizes the PET likelihood function, the present method may be accelerated by the use of TOF information, if available.

B5) Conclusion

This work describes EMAA, the first ever MLEM algorithm for joint estimation of emission activity distribution and photon attenuation map in PET, and suggests a particular GPU based formulation. Joint EMAA estimation converged to the original emission activity distribution and photon attenuation map with root mean square errors of 15% and 9% respectively, which is encouraging in view of possible local likelihood extrema. As mentioned in Section B4, joint MLEM-based EMAA is currently too slow for clinical application. However, the quick separate EMAA estimation suggests it could be accelerated to a clinically relevant speed, by reducing the crosstalk between the emission activity distribution and photon attenuation map, and using OSEM and/or TOF information.

APPENDIX A: DERIVATION OF CONDITIONAL EXPECTATION (10)

The conditional probability of $X_{jk}^{di}$ is given by $$P(X_{jk}^{di}|n_d) = \sum_{\{X_{0N+1}^{di}|X_{0N+1}^{di} \le X_{jk}^{di}, n_d\}} P(X_{jk}^{di}|X_{0N+1}^{di})P(X_{0N+1}^{di}|n_d) \quad (30)$$

Hence, the conditional expectations, $\hat{X}_{jk}^{di}$, are given by $$\hat{X}_{jk}^{di} \equiv E(X_{jk}^{di}|n_d) = \sum_{X_{jk}^{di}=0}^{\infty} X_{jk}^{di} P(X_{jk}^{di}|n_d) = \quad (31)$$

$$\sum_{X_{0N+1}^{di}=0}^{n_d} P(X_{0N+1}^{di}|n_d) \sum_{X_{jk}^{di}=X_{0N+1}^{di}}^{\infty} X_{jk}^{di} P(X_{jk}^{di}|X_{0N+1}^{di}) =$$

$$\sum_{X_{1N+1}^{di}=0}^{n_d} P(X_{0N+1}^{di}|n_d) E(X_{jk}^{di}|X_{0N+1}^{di})$$

The conditional distribution of the variable $X_{0N+1}^{di}$ is given by the following expression:

$$X_{0N+1}^{di}|X_{jk}^{di} \sim Pois(X_{jk}^{di}\gamma_{0j}^{d}\Delta_{kN+1}^{d})$$

Using Bayes' theorem, the conditional distribution of the variable $X_{jk}^{di}$ given by the following expression:

$$P(X_{jk}^{di}|X_{0N+1}^{di}) = \frac{P(X_{0N+1}^{di}|X_{jk}^{di})P(X_{jk}^{di})}{P(X_{0N+1}^{di})} \quad (32)$$

$$= Pois[X_{0N+1}^{di} + \theta_{di}c_{di}(\gamma_{jk}^{d} - \gamma_{0N+1}^{d})]$$

Hence, the conditional expectation $E(X_{jk}^{di}|X_{0N+1}^{di})$ is given by the following expression:

$$E(X_{jk}^{di}|X_{0N+1}^{di}) = X_{0N+1}^{di} + \theta_{di}c_{di}(\gamma_{jk}^{d} - \gamma_{0N+1}^{d}) \quad (33)$$

Moreover, assuming a multinomial distribution for $\{X_{0N+1}^{di}; \Sigma_i X_{0N+1}^{di} = n_d\}$, with a Poisson, as opposed to deterministic, parameter $n_d$, $\{X_{0N+1}^{di}\}$ may be treated as independent Poisson variables:

$$X_{0N+1}^{di} \sim Pois(\theta_{di}c_{di}\gamma_{0N+1}^{di}) \quad (34)$$

Hence:

$$X_{0N+1}^{di}|n_d = X_{0N+1}^{dj}|\sum_j X_{0N+1}^{dj} = Bin\left(n_d, \frac{\theta_{di}c_{di}}{\sum_j \theta_{dj}c_{dj}}\right) \quad (35)$$

Substitution of Eqs. (33) and (35) into Eq. (31), yields Eq. (10):

$$\hat{X}_{jk}^{di} = \theta_{di}c_{di}\left(\frac{n_d}{\sum_j \theta_{dj}c_{dj}} + \gamma_{jk}^{d} - \gamma_{0N+1}^{d}\right)$$

APPENDIX B: DERIVATION OF THE PHOTON ATTENUATION UPDATE EQUATION (12)

For completeness, the following appendix derives the photon attenuation update equations with variable, as opposed to constant, LOR/cell intersection lengths, $1_{di}$. In order to maximize the expectation of likelihood (8) in Eq. (9), it was rearranged as follows:

$$E(L^*(\theta,\mu)|n;\theta^m,\mu^m) = \sum_{di}\left\{-\theta_{di}c_{di} + \right. \quad (36)$$

-continued $$\hat{X}_{ii}^{di}\ln\theta_{di} + \left[\hat{X}_{ii}^{di} - \hat{X}_{i-1i+1}^{di} + \sum_j\{(\hat{X}_{ij+1}^{dj} - \hat{X}_{i-1j+1}^{dj})I_{j>1} + \right.$$

$$\left.(\hat{X}_{0i}^{dj} - \hat{X}_{0i+1}^{dj})I_{j<i}\}\right]\ln(1 - e^{-\mu_{di}l_{di}}) -$$

$$\left[\hat{X}_{i-1i+1}^{di} + \sum_j\{\hat{X}_{i-1j+1}^{dj}I_{j>i} + \hat{X}_{0i+1}^{dj}I_{j<i}\}\right]\mu_{di}l_{di}\}$$

Since this expression is additively separable, equating its $\mu_\xi$ derivatives to zero results in a series of independent one dimensional equations, of the following form:

$$\sum_{di}I_{di\xi}l_{di}\left[\frac{1}{e^{\mu_\xi^{m+1}l_{di}} - 1}\Delta\hat{M}_i^{dm} - \hat{M}_i^{dm}\right] = 0 \quad (37)$$

where using the notations of Algorithm 1, and omitting the iteration index m:

$$\Delta\hat{M}_i^d \equiv \left[ \right. \quad (38)$$

$$\sum_j\hat{X}_{ij}^{dj} - \hat{X}_{i-1j+1}^{dj} + (\hat{X}_{0i}^{dj} - \hat{X}_{0i+1}^{dj})I_{j<i} + (\hat{X}_{ij+1}^{dj} - \hat{X}_{i-1j+1}^{dj})I_{j<i}\right] =$$

$$[1 - e^{-\mu_{di}l_{di}}]\sum_j\theta_{dj}c_{dj}(\gamma_{0i}^dI_{j<i} + \gamma_{ij+1}^dI_{j\geq i})$$

$$\hat{M}_i^d \equiv \sum_j\hat{X}_{i-1j+1}^{dj}I_{j\geq i} + \hat{X}_{0i+1}^{dj}I_{j<i} = \quad (39)$$

$$n_d - \gamma_{0N+1}^d\sum_j\theta_{dj}c_{dj} + e^{-\mu_{di}l_{di}}\sum_j\theta_{dj}c_{dj}(\gamma_{0i}^dI_{j<i} + \gamma_{ij+1}^dI_{j\geq i})$$

With a Cartesian grid, rather than that of Section B2d, Eq. (37) does not have a closed solution due to the variable $l_{di}$. Thus, it has to be either approximated, or solved numerically. However, the constant $l_{di}=1$ LOR oriented grid of Section B2a results in the following explicit solution:

$$\mu_\xi^{m+1} = \frac{1}{l}\ln\left(1 + \frac{\sum_{di}I_{di\xi}\Delta\hat{M}_i^{dm}}{\sum_{di}I_{di\xi}\hat{M}_i^{dm}}\right) \quad (40)$$

Note that the numerator in Eq. (40), $\Sigma_{di}I_{di\xi}\Delta\hat{M}_i^{dm}$, corresponds to an expected number of photons scattered inside voxel $\xi$, while the denominator, $\Sigma_{di}I_{di\xi}\hat{M}_i^{dm}$, corresponds to that of unscattered photons.

The invention claimed is:

1. A method of image reconstruction for positron emission tomography (PET), the method comprising:
   obtaining raw PET data from a PET scanner;
   analyzing the raw PET data to provide estimates of both emission activity and photon attenuation;
   wherein the analyzing the raw PET data comprises maximum likelihood expectation maximization (MLEM);
   wherein a first set of MLEM coordinates relates to voxels in a PET image;
   wherein a second set of MLEM coordinates is defined by a partition of each line of response (LOR) into LOR cells having equal length l;
   wherein MLEM computations assume all intersections between LOR cells and voxels have an intersection length of l.

2. The method of claim 1, wherein the MLEM is performed on a graphics processing unit (GPU).

3. The method of claim 1, wherein parameters for MLEM update computations are performed by traversing lines of response in both directions.

4. The method of claim 1,
   wherein an iteration of MLEM update computations comprises the steps of expectation computation followed by maximization, and wherein:
   $\xi$ is a voxel index,
   d is a line of response (LOR) index,
   i is a cell index,
   $n_d$ is the number of counts on LOR d,
   m is an iteration index,
   $\mu$ is photon attenuation per unit length,
   $\theta$ is emission activity per unit volume,
   $c_{di}$ is a cell(i)/LOR(d) system matrix element times the cell volume,
   $N_d$ is the number of cells on LOR d,
   $\xi(d,i)$ is the index of the voxel that contains the center of LOR cell i in LOR d,
   $\theta_{di}$ is an abbreviation for $\theta_{\xi(d,i)}$,
   $\mu_{d,i}$ is an abbreviation for $\mu_{\xi(d,i)}$,
   L is likelihood,
   A, G, R, S, D, and K are auxiliary quantities computed in the MLEM updates,
   $I_{di\xi}=1$ if the center of LOR cell i of LOR d is in voxel $\xi$,
   $I_{di\xi}=0$ if the center of LOR cell i of LOR d is not in voxel $\xi$, and $$P_\xi = \sum_{di}I_{di\xi}c_{di}$$

is a normalization factor;
   wherein the expectation computation comprises executing the following method:

```
L ← 0 ;
for all voxels ξ do
    A_ξ ← 0 ;
    G_ξ ← 0 ;
    R_ξ ← 0 ;
end for
for all detected LORs d do
    K ← 0 ;
    D ← 0 ;
    for LOR cell i = 1 to N_d do
        G_ξ(d,i) ← G_ξ(d,i) + n_d ;
        D ← D + μ_di^m ;
        K ← K + θ_di^m c_di ;
    end for
    L ← n_d(ln K − lD) ;
    for LOR cell i = 1 to N_d do
        A_ξ(d,i) ← A_ξ(d,i) + c_di n_d/K ;
    end for
end for.
```

5. The method of claim 4, wherein the maximization comprises executing the following method:

```
for all LORs d do
    K ← 0;
    D ← 0;
    for LOR cell i = 1 to N_d do
        R_{ξ(d,i)} ← e^{-lD}K;
        D ← D + μ_{di}^m;
        K ← K + θ_{di}^m c_{di};
    end for
    L ← L - e^{-Dl}K;
    S ← 0;
    for LOR cell i = N_d to 1 do
        A_{ξ(d,i)} ← A_{ξ(d,i)} + c_{di}(1 - e^{-lD}) ;
        G_{ξ(d,i)} ← G_{ξ(d,i)} - e^{-lD}K;
        R_{ξ(d,i)} ← R_{ξ(d,i)} + θ_{di}^m c_{di} + S;
        S ← (θ_{di}^m c_{di} + S)e^{-lμ_{di}^m};
    end for
end for
for all voxels ξ do
    θ_ξ^{m+1} ← θ_ξ^m A_ξ/P_ξ;
    μ_ξ^{m+1} ← (1/l) ln[ 1 + ((1 - e^{-lμ_ξ^m})R_ξ) / (G_ξ + e^{-lμ_ξ^m} R_ξ) ];
end for.
```

\* \* \* \* \*